(12) United States Patent
Abbott et al.

(10) Patent No.: US 7,183,433 B2
(45) Date of Patent: Feb. 27, 2007

(54) IONIC LIQUIDS AND THEIR USE AS SOLVENTS

(75) Inventors: Andrew P. Abbott, Leicester (GB); David L. Davies, Leicester (GB); Glen Capper, Exmouth (GB); Raymond K. Rasheed, Brampton (GB); Vasuki Tambyrajah, Dehiwala (LK)

(73) Assignee: Scionix Limited, London (GB)

( * ) Notice: Subject to any disclaimer, the term of this patent is extended or adjusted under 35 U.S.C. 154(b) by 204 days.

(21) Appl. No.: 10/381,060

(22) PCT Filed: Sep. 26, 2001

(86) PCT No.: PCT/GB01/04300

§ 371 (c)(1), (2), (4) Date: Jul. 7, 2003

(87) PCT Pub. No.: WO02/26701

PCT Pub. Date: Apr. 4, 2002

(65) Prior Publication Data

US 2004/0097755 A1 May 20, 2004

(30) Foreign Application Priority Data

Sep. 27, 2000 (GB) ................................ 0023706

(51) Int. Cl.
*C07C 211/00* (2006.01)
(52) U.S. Cl. ..................... 564/282; 564/291
(58) Field of Classification Search ................ 564/281, 564/282, 284, 291, 292, 293, 294
See application file for complete search history.

(56) References Cited

U.S. PATENT DOCUMENTS

| | | | |
|---|---|---|---|
| 5,731,101 | A | 3/1998 | Sherif et al. |
| 6,573,405 | B1 | 6/2003 | Abbott et al. |
| 2004/0097755 | A1* | 5/2004 | Abbott et al. |

FOREIGN PATENT DOCUMENTS

JP 08085900 * 4/1996

OTHER PUBLICATIONS

Saito et al., Complexes of Urea and Symmetrical Tetraalkylammonium Halides, JACS, 88:22, 5107-5112.*
Mak, thiourea-Halide Lattices. Part 1., Journal of Inclusion Phenomena and Molecular recognition Chemistry 8:199-207, 210-214, 1990.*
Kazakov, Fiziologicheski Aktivnye Veshchestva (1988), 20, 40-4, (Chemical Abstracts online Abstract).*
Vyzk et al., Agrochemia (Bratislava) (1971), 11(10), 302-3.*
Saito, Shuji et al., "Complexes of urea and symmetrical tetraalkylammonium halides," J. Am. Chem. Soc., vol. 88 (No. 22), p. 5107-5112, (1966).
O. Kristiansson et al., "Interaction between methanol and Cl-, Br-, I-, NO3-, CLO4-, SO3CF3- and PF6- Anions studies by FRIR Spectroscopy," Acta Chemica Scandinavica, vol. 51 (1997), p. 270-273, (1997).
Q Li et al., "Hydrogen-bonded Urea-Anion Host latticies.6. New inclusion compounds of urea with tetra-n-propylammonium halides," Acta Cryst., Intern'l Union of Cryst (Great Britain), vol. B54, 1998, p. 180-192, (1998).
Jahresbericht Ueber Die Fortschritte Der Chemie Und Verwandter Teile Anderer Wissenschafter, p. 531-547.
Q. Li, et al., "Tetra-n-butylammonium Chloride Thiourea (1/2) a layer type inclusion compound," Acta Crystallographica, Internat'l Union of Cryst (Great Britain), vol. C52, 1996, p. 2830-2832, (1996).
Mak, Thomas C.W., "Thiourea-halide lattices.I. Crystal Structures of (n-C4H9)4N+F-.3(NH2)2CS, (n-C4H9)3(CH3)N+X-.2(NH2)2CS (X=Cl, Br), and (n-C3H7)4N+1-.(NH2)2CS," Journ. of Inclusion Phenomena & Molecular Recognition in Chemistry, (Netherlands), p. 199-214, (1990).

* cited by examiner

*Primary Examiner*—Shaojia Anna Jiang
*Assistant Examiner*—Karl Puttlitz
(74) *Attorney, Agent, or Firm*—Bacon & Thomas, PLLC

(57) ABSTRACT

Ionic compounds with a freezing point of up to 100° C. are formed by the reaction of an one amine salt of formula (I) $R^1R^2R^3R^4N^+X^-$, such as choline chloride with an organic compound (II) capable of forming a hydrogen bond with X; such as urea, wherein the molar ration of I to II is from 1:1.5 to 1:2.5. $R^1$, $R^2$, $R^3$ and $R^4$ may be H, optionally substituted $C_1$ to $C_5$ alkyl, optionally substituted $C_6$ to $C_{10}$ cycloalkyl, optionally substituted $C_6$ to $C_{12}$ aryl, optionally substituted $C_7$ to $C_{12}$ alkaryl, or $R^1$ and $R^2$ taken together may represent a $C_4$ to $C_{10}$ optionally substituted alkylene group, thereby forming with the N atom of formula I a 5 to 11-membered heterocyclic ring and all of $R^1$, $R^2$, $R^3$ and $R^4$ are not identical, $X^-$ may be $NO_3^-$, F, $Cl^-$, $Br^-$, $I^-$, $BF_4^-$, $ClO_4^-$, $CN^-$, $SO_3CF_3^-$, or $COOCF_3^-$. The ionic compounds are useful as solvents, and electrolytes for example in electroplating, electrowinning, and electropolishing, and as catalysts.

20 Claims, No Drawings

IONIC LIQUIDS AND THEIR USE AS SOLVENTS

This invention relates to ionic compounds and methods for their preparation. In particular the invention relates to ionic compounds which are liquid at relatively low temperatures, i.e. generally below about 100° C., and preferably below about 60° C. and more preferably which are liquid at or near to ambient temperature.

There is much current interest in the field of ionic liquids. Such systems, which are examples of molten salts, have a number of interesting and useful chemical properties, and have utility, for example, as highly polar solvents for use in preparative chemistry, and as catalysts. They also have particular application in electrochemistry, for example in batteries, fuel cells, photovoltaic devices and electrodeposition processes, for example in baths for the electroplating of metals.

Generally speaking, ionic liquids have very low vapour pressure and thus, in contrast to many conventional solvents, are very advantageous in that they produce virtually no hazardous vapours. They are therefore advantageous from a health, safety and environmental point of view.

One such system which has been known for many years is that formed from 1-ethyl-3-methylimidazolium chloride-aluminium chloride (EMIC-AlCl$_3$). This system is a thermally stable liquid between −100° C. to ca. 200° C., dependent on the molar ratio of EMIC to AlCl$_3$ utilised.

Such EMIC-AlCl$_3$ systems have been used extensively as solvents for various ionic reactions and as electrolytes, as described, for example in U.S. Pat. No. 5,525,567, FR-A-2611700, FR-A-2626572, WO95/21872, and EP-A-838447. There are a number of difficulties in utilising such compounds. These arise principally from their cost, and from their water sensitivity.

In recent years, other ionic compounds have been made which are liquid at relatively low temperatures. For example, U.S. Pat. No. 4,764,440 discloses low temperature molten compositions, formed by reacting, for example, trimethylphenylammonium chloride with aluminium trichloride. The resulting ionic compound has a low freezing point (around −75° C.), but suffers from the same water sensitivity as EMIC-AlCl$_3$, because of the presence of aluminium trichloride.

Proposals have been made to utilise other metal halides, in place of aluminium trichloride. For example, U.S. Pat. No. 5,731,101 discloses the use of iron and zinc halides as the anion portion of an ionic liquid composition. The cation portion is formed by an amine hydrohalide salt, of the formula R$_3$N.HX (X=halide). This reference indicates however that the aluminium compounds are preferred.

PCT/GB00/01090 discloses ionic liquids, formed by the reaction of quaternary ammonium compounds such as choline chloride with halides of zinc, tin, or iron.

SAITO, SHUJI ET AL: "Complexes of urea and symmetrical tetraalkylammonium halides" J. AM. CHEM. SOC. (1966), 88(22), 5107–12 discloses complexes of urea and symmetrical Tetraalkylammonium halides. The complexes are crystalline, and there is no disclosure of the use of asymmetrical ammonium compounds, nor of the use of liquids formed from such complexes as solvents.

KOICHI TANAKA ET AL: "Molecular aggregation of alkyltrimethylammonium bromide and alcohol in the solid state" MOL. CRYST. LIQ. CRYST., Vol. 277, 1996, pages 139–143 is concerned with the separation of primary alcohols from mixtures of primary and secondary alcohols, by complexation with quaternary ammonium bromides with an alkyl chain length of at least 10.

O. KRISTIANSSON ET AL: "Interaction between methanol and Cl−, Br−, I−, N03, C104−, S03CF3 and PF6− Anions studied by FTIR spectroscopy" ACTA CHEMICA SCANDINAVICA, vol. 51, 1997, pages 270–273 discloses compounds formed between quaternary ammonium cations and methanol KEIJU SAWADA ET AL: "X-Ray analyses of complexes formed between surfactants and aromatic compounds. I. A common structural pattern of complexes" BULLETIN OF THE CHEMICAL SOCIETY OF JAPAN., Vol. 71, 1998, pages 2109–2118 discloses the production of various solid materials from quaternary amines and a variety of aromatic compounds NEGITA ET AL: "14N Nuclear quadropole resonance of the molecular complexes of urea" BULLETIN OF THE CHEMICAL SOCIETY OF JAPAN., Vol. 54, 1981, pages 391–393 discloses solid complexes of urea with quaternary amines.

MASOOD A. KAHN: "Hydrogen bonding and crystal packing trends in tetraalkylammonium halide-catechol complexes: Synthesis, spectroscopic and crystal structure studies of Me4NCl-catechol, Et4NCl-catechol, Et4NBr-catechhol and Pr4NBr-catechol complexes."

JOURNAL OF MOLECULAR STRUCTURE, Vol. 145, 1986, pages 203–218 discloses crystalline compounds prepared from symmetrical amines and catechol U.S. Pat. No. 5,731,101 A (LACROIX CHRISTINE P M ET AL) 24 Mar. 1998 (Mar. 4, 1988) and MASOOD A. KAHN ET AL: "novel hydrogen bonding in crystalline tetra-n-butylammonium salts of catechol halides" CANADIAN JOURNAL OF CHEMISTRY, Vol. 63, 1985, pages 2119–2122 disclose low temperature ionic liquid compositions prepared from aluminium trichloride and triethylamine Q. LI; T. C. W. MAK: "Novel inclusion compounds consolidated by host-host and by host-guest hydrogen bonding: complexes of thiourea with (2-hydroxyethyl)trimethylammonium carbonate and oxalate" discloses solid inclusion compounds prepared from thiourea and quaternary ammonium compounds.

We have now found that it is possible to form compounds which are liquid at temperatures of 100° C. or below by reacting an amine salt, preferably a quaternary amine salt, with an organic material, preferably one which is a solid at 20° C., and which is capable of forming a hydrogen bond with the anion of the amine salt. Compounds suitable for forming such hydrogen bonds include amides, such as urea, thiourea, and acetamide, carboxylic acids such as oxalic acid, benzoic acid and citric acid, alcohols, phenol, and substituted phenols, as well as sugars such as fructose. Although it is not intended to be bound by any particular theory of operation, it is believed that hydrogen bonding of the organic compound with the anion of the ammonium compound allows charge delocalisation, which stabilises the liquid form of the compound.

According to the invention, there is provided an ionic compound, having a freezing point of up to 100° C. preferably up to 60° C., formed by the reaction of at least one amine salt of the formula $$R^1R^2R^3R^4N^+X^- \qquad (I)$$

with at least one organic compound (II) which is preferably a solid at 20° C., and which is capable of forming a hydrogen bond with X−, wherein $R^1$ $R^2$ $R^3$ and $R^4$ are each independently:

H, optionally substituted $C_1$ to $C_5$ alkyl, optionally substituted $C_6$ to $C_{10}$ cycloalkyl, optionally substituted $C_6$ to $C_{12}$ aryl optionally substituted $C_7$ to $C_{12}$ alkaryl, or wherein $R^1$ and $R^2$ taken together represent a $C_4$ to $C_{10}$ optionally substituted alkylene group, thereby forming with the N atom of formula I a 5 to 11-membered heterocyclic ring, $X^-$ is $NO_3^-$, F, $Cl^-$, $Br^-$, $I^-$, $BF_4^-$, $ClO_4^-$, $CN^-$, $SO_3CF_3^-$, or $COOCF_3^-$, and wherein the term "optionally substituted" means that the group in question may or may not be substituted with at one or more groups (preferably from 0 to 6 groups) selected from OH, SH, $SR^5$, Cl, Br, F, I, $NH_2$, CN, $NO_2$, $COOR^5$, CHO, $COR^5$ and $OR^5$, wherein $R^5$ is a $C_1$ to $C_{10}$ alkyl or cycloalkyl group, and wherein the molar ratio of I to II is from 1:1.5 to 1:2.5.

Compound II is preferably a compound of the formula $R^6COOH$, $R^7R^8NH$, $R^9CZNH_2$, or $R^{10}OH$, wherein:

$R^6$, $R^7$, $R^8$, $R^{10}$ are each H, a $C_1$–$C_8$ alkyl group, an aryl group, or a $C_7$–$C_{12}$ alkaryl group optionally substituted with from 0 to 6 groups selected from OH, $SR^5$, Cl, Br, F, I, $NH_2$, CN, $NO_2$, $COOR^5$, $COR^5$ and $OR^5$, wherein $R^5$ is H, a $C_1$ to $C_{10}$ alkyl or cycloalkyl group $R^9$ is a group as defined for $R^6$, or $NHR^{11}$, wherein $R^{11}$ is H or a $C_1$–$C_6$ alkyl group, and Z is O or S.

Preferably, Compound II is urea, aniline, or a substituted aniline, a $C_1$–$C_6$ aliphatic acid, a $C_1$–$C_6$ aliphatic amine, a $C_1$–$C_6$ hydroxy aliphatic acid, or a dicarboxylic acid of the formula $HOOC(CH_2)_nCOOH$, wherein n is 0 or 1 acetamide, a phenol or a substituted phenol, an alkylene glycol, or citric acid. Most preferably, compound II is urea, acetamide, oxalic acid dihydrate, phenol, ethylene glycol, or citric acid.

The Compounds I and II are mixed in a molar ratio of from 1:1.5 to 1:2.5, preferably about 1:2. In general, the amine salts (I) used in the preparation of the ionic compounds according to the invention are preferably asymmetric, i.e., the substituent groups ($R^1$, $R^2$, $R^3$ and $R^4$) are preferably not all identical.

The preferred amine salts of Formula I are the same as those which are preferred in PCT/GB00/01090, namely ones where $R^4$ is a $C_1$ to $C_{10}$ alkyl or a cycloalkyl group, substituted with at least one group selected from OH, Cl, Br, F, I, $NH_3$, CN, $NO_2$, $OR^5$, $COOR^5$, CHO, and $COR^5$. It is particularly preferred that $R^4$ is an ethyl group, substituted with one or more of hydroxyl, chlorine, or an ester (i.e. that the substituent $R^4$ is derived from choline, chlorocholine, or a chlorocholine ester). Specific examples of $R^4$ groups which have been found to be suitable are 2-hydroxyethyl, 2-bromoethyl, 2-chloroethyl, 2-acetoethyl, N-decyl, cyclohexyl, 2-hydroxy 3-chloropropyl, and 3-bromopropyl. In a further preferred embodiment, the amine cation is chiral.

The counter-ion $X^-$ of compound (I) is preferably halide, for example bromide or chloride.

The ionic compounds according to the invention may be prepared simply by mixing the amine salt (I), with the hydrogen bond donor (II). The reaction is generally endothermic, and is usually carried out by heating, for example to a temperature of 100° C. or more.

The ionic compounds according to the invention may be utilised for a wide range of purposes, for example as electrolytes in electrochemical devices such as batteries or fuel cells, in photovoltaic or electrochromic devices, and in electrochemical deposition electropolishing, or electro-refining. The compounds find particular application for carrying out applications where a polar but non-aqueous solvent is required. They may also be employed as inert media, for dissolving ionic species such as transition metal complexes, and, either alone, or after complexing with other metal ions, as catalysts, or as chemical reagents. They may also be used for extracting a solute from an immiscible solvent.

The ionic compounds according to the invention also may be used as an alternative to the traditional mixtures of strong acids as solvents for the electropolishing of metals, for example stainless steel and aluminium. At least the preferred compounds according to the invention are more environmentally friendly than the traditional acid mixtures used for electropolishing stainless steel, as well as being cheap and reusable. In addition they can result in lower power consumption and reduced local environmental hazards in the workplace, for example those caused by gas evolution such as 'misting' of conventional acid mixtures.

A number of preferred embodiments of the invention are illustrated in the following examples. The composition of all of the products was characterised using $^1H$ NMR spectroscopy, and their ionic character was characterised by conductivity measurements, using a Jenway 4071 conductivity meter and temperature probe. All of the compounds had an electrical conductivity of at least 10 μS cm$^{-1}$ at 10° C. above their freezing point. The starting materials used in the Examples were all anhydrous materials, and were dried under vacuum for 2 hours prior to use.

EXAMPLE 1

Choline chloride (a quaternary ammonium compound of the general formula I above, in which $R^1$, $R^2$, and $R^3$ are methyl, $R^4$ is $C_2H_4OH$, and $X^-$ is $Cl^-$) 1.40 g (0.01 mol) was added to 1.2 g of urea (0.02 mol) in a laboratory test tube. The mixture was heated to a temperature of 70° C. for a period of 20 min, to produce a clear colourless liquid. The melt was allowed to cool at a rate of approximately 1° C. per minute, and the temperature recorded at which initial crystal formation was observed and recorded as the freezing point. (For all eutectic mixtures, complete freezing of the composition takes place at a temperature much lower than that of initial crystal formation, but the solidification is slow, and in some cases the materials can remain as gels for several days before solidification). The conductivity of the 2:1 Urea/ choline chloride ionic liquid at 19° C. was 338 μS cm$^{-1}$. The freezing point of the mixture was 12° C.

EXAMPLES 2 TO 15

The procedure of Example 1 was repeated, using 0.02 mols of the compounds "II" identified in Table 1, in place of urea. The results are shown in Table 1. In each case, the heating was carried out until a clear melt was formed, and the freezing point was then determined by the first appearance of crystal formation, at a cooling rate of 1° C. per minute.

TABLE 1

| Example No | Compound II | Fr Pt. of Melt (° C.) |
|---|---|---|
| | Amides | |
| 1 | Urea, $NH_2CONH_2$ | 12 |
| 2 | Acetamide, $CH_3CONH_2$ | 51 |
| 3 | Thiourea, $NH_2CSNH_2$ | 69 |

TABLE 1-continued

| Example No | Compound II | Fr Pt. of Melt (° C.) |
|---|---|---|
| 4 | Salicylamide, o-HOC$_6$H$_4$CONH$_2$ | 91 |
| 5 | Benzamide, C$_6$H$_5$CONH$_2$ | 92 |
| | Carboxylic acids | |
| 6 | Glyoxylic acid | below 0 |
| 7 | Malonic acid, HOOCCH$_2$COOH | below 0 |
| 8 | Oxalic acid, HOOCCOOH | 48 |
| 9 | Benzoic acid, C$_6$H$_5$COOH | 95 |
| | Alcohols | |
| 10 | Benzyl alcohol, C$_6$H$_5$CH$_2$OH | 61 |
| 11 | Phenol C$_6$H$_5$OH | −30 |
| 12 | p - Methyl phenol | −10 |
| 13 | o - Methyl phenol | −8 |
| 14 | m - Methyl phenol | Below −35 |
| 15 | p - Chloro phenol | Below −35 |
| 16 | D-Fructose | 5 |
| 17 | Vanilin p-HO m OCH$_3$C$_6$H$_3$CHO | 42 |
| 18 | p - Amino phenol | 93 |
| | Amines | |
| 19 | Aniline | 44 |
| 20 | Hydroxylamine hydrochloride | 81 |

In order to demonstrate that the formation of the liquid ionic compound is the result of hydrogen bonding between Compound II and the chloride anion, attempts were made to prepare similar materials using various other starting materials, using the same procedure as Example 1. The results are shown in Table 2, as Comparative Examples 1 to 8.

In the same manner as described in Example 1, compounds were prepared from choline chloride (0.01 moles) and each of the compounds shown in Table 1A (0.02 moles). The freezing point of the resulting compound is shown in Table 1A By contrast, the substances indicated in Table 2A, when substituted in the same molar quantity for the urea of Example 1 did not give an ionic liquid with a freezing point of 100° C. or less.

TABLE 2

| Comp Ex. No | Compound II | Fr Pt. of Melt (° C.) |
|---|---|---|
| | Amides | |
| 1 | Dimethylurea, NHCH$_3$CONHCH$_3$ | 149 |
| | Esters and Ethers | |
| 2 | Anisole C$_6$H$_5$OCH$_3$ | no melt formed. |
| 3 | 4-Iodoanisole | no melt formed. |
| 4 | Diethyloxalate (C$_2$H$_5$OOC)$_2$ | no melt formed. |
| 5 | Diethylmalonate | no melt formed. |
| | Aldehydes and Ketones | |
| 6 | Benzyl methyl ketone | no melt formed |
| | Other | |
| 7 | Hexachloroethane | no melt formed. |
| 8 | Cyclohexane | no melt formed |

TABLE 1A

| Compound II | Fr Pt. of Melt (° C.) |
|---|---|
| Amides | |
| Allyl urea | 9 |
| Urea/H$_2$O$_2$ complex | 19 |
| Carboxylic acids | |
| Trifluoroacetic acid | Below −40 |
| Trichloroacetic acid | −24 |
| Citric acid | 26 |
| Mandelic acid | 33 |
| Valeric acid | 22 |
| Tartaric acid | 74 |
| Phenyl acetic acid | −5 |
| m-nitrobenzoic acid | 85 |
| p-hydroxybenzoic acid | 97 |
| Glutamic acid | 13 |
| m-aminobenzoic acid | 39 |
| Alcohols | |
| Ethanediol | −20 |
| Triethanolamine | −24 |
| 2-chloroethanol | 6 |
| Vanillin | 17 |
| p-hydroxybenzaldehyde | 29 |
| Sugars | |
| D(-) Fructose | 5 |
| D-glucose | 14 |
| Amines | |
| Diaminoethane | 29 |
| 1,2-diaminopropane | 63 |
| Misc. | |
| Water | 11 |
| p-toluenesulphonic acid monohydrate | 27 |
| Dibenzenesulfonamide | 39 |

TABLE 2A

| Compound II | Fr Pt. of Melt (° C.) |
|---|---|
| Carboxylic acids | |
| salicylic acid | 103 |
| trans-cinnamic acid | 101 |
| 3,5-dinitrobenzoic acid | 104 |
| nicotinic acid | 126 |
| stearic acid | no melt formed |
| hippuric acid | no melt formed |
| oleic acid | no melt formed |
| terephthalic acid | no melt formed |
| Alcohols | |
| 9-Anthracenemethanol | no melt formed. |
| Ethanol | no melt formed. |
| Propan-2-ol | no melt formed. |
| Mannitol | 108 |
| 8-hydroxyquinoline | no melt formed |
| 2-methyl salicylate | no melt formed |
| 2-phenyl salicylate | no melt formed |
| Sugars | |
| Lactose | no melt formed |
| Saccharin | no melt formed |
| Amines | |
| Pyridine | no melt formed. |
| Benzyl amine | no melt formed. |
| triethylamine | no melt formed |
| Esters and ethers | |
| Ethyl cinnamate | no melt formed |
| Aldehydes and ketones | |
| Benzaldehyde | no melt formed. |

TABLE 2A-continued

| Compound II | Fr Pt. of Melt (° C.) |
|---|---|
| Amino acids | |
| Glycine | no melt formed. |
| Alanine | no melt formed. |
| Lysine | no melt formed |
| Phenylalanine | no melt formed |
| Misc. | |
| Ferrocene | no melt formed. |
| Sarcosine | No melt formed. |
| Tetrabutylammonium hydrogen sulphate | 159 |
| 1,2-dichloroethane | No melt formed. |
| Uric acid | No melt formed |
| Nitroethane | No melt formed. |
| Glycerol triacetate | No melt formed |

The results in Tables 1, 2, 1A and 2A demonstrate that many but not all compounds which are in principle capable of donating a hydrogen atom to a hydrogen bond are capable of forming ionic liquids with choline chloride, by the method of Example 1. In general, the compounds which are form the most useful ionic compounds (i.e., those with the lowest freezing points) are ones in which the "Compound II" employed has a relatively low freezing point, for example, less than 150° C., preferably less than 100° C., more preferably less than 50° C., and yet more which have a freezing point of 20° C., or less (i.e., which are solid at ambient temperature).

An additional factor which has an important bearing upon whether a particular hydrogen bond donor compound (II) is capable of forming an ionic liquid having a freezing point of 100° C. or less is the difference between the degree of structure of the compound in the solid and liquid states. Compounds capable in principle of forming a hydrogen bond, but in which difference between the degree of structure in the solid and liquid states is low are generally not preferred. For example long chain aliphatic acids which have a low freezing point but a low degree of structure in the solid state are generally unsatisfactory. Likewise, compounds which are highly ordered in the liquid state (such as trifluoroaceticacid) are generally favoured.

Yet a further factor with important bearing upon whether a particular hydrogen bond donor compound (II) is capable of forming an ionic liquid having a freezing point of 100° C. or less is the presence of different types of functional groups capable of acting as hydrogen bond donors. It is strongly preferred that only one type of functional group capable of acting as hydrogen bond donor is present in the compounds II. For Example, although two carboxylic acid groups may be present, compounds containing both a COOH group and an $NH_2$ group, (amino acids) are generally not preferred.

One of skill in the art will generally be capable of selecting a suitable hydrogen bond donor for the purposes of the invention, based on the foregoing criteria, and the specific Examples herein.

EXAMPLE 16

The effect of changing the nature of the anion $X^-$ was investigated, by repeating the procedure of Example 1, using choline nitrate, and choline tetrafluoroborate (0.01 mol) instead of choline chloride, in the procedure of Example 1. The freezing points of the resulting compounds are shown in Table 3.

TABLE 3

| Example No | $X^-$ | Fr Pt./° C. |
|---|---|---|
| 21 | $BF_4$ | 67 |
| 22 | $NO_3$ | 4 |

EXAMPLES 23 TO 41

The effect was investigated of substituting various other amine salts of Formula I, for the choline chloride of Example 1. In each case, 0.01 mol of the amine salt, as shown in Table 4, was heated with 0.02 mol of urea, until a clear melt was formed. Freezing points were measured by cooling, as before. The freezing points are shown in Table 4.

TABLE 4

| Ex. | $R^1$ | $R^2$ | $R^3$ | $R^4$ | $X^-$ | Fr. Pt./° C. |
|---|---|---|---|---|---|---|
| 1 | Me | Me | Me | $C_2H_4OH$ | Cl | 12 |
| 23 | Me | Me | Benzyl | $C_2H_4OH$ | Cl | −33 |
| 24 | Me | Me | Et | $C_2H_4OH$ | Cl | −38 |
| 25 | Me | Me | Me | Benzyl | Cl | 26 |
| 26 | Me | Me | Me | $C_2H_4OCOMe$ | Cl | −14 |
| 27 | Me | Me | Me | $C_2H_4Cl$ | Cl | 15 |
| 28 | Me | Me | Me | $ClCH_2CHOHCH_2$ (R) | Cl | 65 |
| 29 | Me | Me | Me | $ClCH_2CHOHCH_2$ (S) | Cl | 83 |
| 30 | Me | H | H | H | Cl | 33 |
| 31 | Me | Me | H | H | Cl | 29 |
| 32 | Et | Et | Et | H | Cl | 95 |
| 33 | Et | Et | Et | Benzyl | Cl | 36 |
| 34 | Me | Benzyl | $C_2H_4OH$ | $C_2H_4OH$ | Cl | −6 |
| 35 | Me | H | H | $CH_2COOH$ | Cl | −3 |
| 36 | Me | Me | Me | $BrC_2H_4$ | Br | 84 |
| 37 | Me | Me | Me | $C_2H_4F$ | Br | 55 |
| 38 | Me | Me | Me | $Me(CH_2)_{11}$ | Br | 92 |
| 39 | Et | Et | Et | Me | Br | 9 |
| 40 | Et | Et | Et | Benzyl | $BF_4$ | 59 |
| 41 | Me | Me | $C_2H_4OH$ | $C_2H_4OH$ | I | 46 |

Comparative Examples 9 TO 15

In the same way, salts of a symmetrical amine, as well as other amines of relatively high molecular weight were investigated, the results are shown in Table 5, as comparative examples 9 to 12. These results demonstrate that unsymmetrical amine salts ($R_1R_2R_3R_4$ are not all identical) of relatively low molecular weight, are preferred.

TABLE 5

| Comp | | R1 | R2 | R3 | R4 | X− | F Pt./° C. |
|---|---|---|---|---|---|---|---|
| 9 | $Bu_4N$ | Bu | Bu | Bu | Bu | Cl | 112 |
| 10 | $Me(CH_2)_{13}(Me)_3N$ | Me | Me | Me | $Me(CH_2)_{13}$ | Br | no melt formed |
| 11 | $Me(CH_2)_{17}(Me)_3N$ | Me | Me | Me | $Me(CH_2)_{17}$ | Br | no melt formed |
| 12 | $Hex(Et)_3N$ | Et | Et | Et | n-hexyl | Br | 108 |

EXAMPLES 42 TO 44

The effect of varying the anion $X^-$ was investigated, using tetraethylammonium salts of various anions, in combination with urea, in the method of Example 1. The results are shown in Table 6.

TABLE 6

| Example | Compound I cation | X⁻ | F Pt./° C. |
|---|---|---|---|
| 42 | (Et)₄N | ClO₄ | 99 |
| 43 | (Et)₄N | O₃SCF₃ | 59 |
| 44 | (Et)₄N | CN | 72 |
| Comp. 25 | (Et)₄N | BF₄ | 130 |
| Comp 26 | (Et)₄N | MeC₆H₄SO₃ | 107 |
| Comp 27 | (Et)₄N | Br | 113 |

Comparison of Example 21 with Comparative Example 25 illustrates broadly that asymmetrical amines are preferred.

Miscibility Tests

The miscibility of the material prepared in Example 1 with a number of common solvents was investigated. It was found to be miscible with methanol, DMSO, and water, and to form two layers with acetone, acetonitrile, acetophenone, bromobenzene, dichloroethane, diethylether, ethylacetate, hexane, propylene carbonate, and toluene. With THF, a white precipitate was formed.

EXAMPLE 45

Use of Ionic Liquids as Battery Electrolytes

Low freezing point ionic liquids prepared from compound II and amine salts can be used as electrolytes in batteries. Two such examples are described below. In the first, 7 ml of the material of Example 1 (2:1 urea-choline chloride) was prepared and poured into separated compartments of a small glass cell. The compartments were separated by glass frit and each contained 3.5 ml of ionic liquid. The cell was suspended in an oil bath so that the liquid temperature was maintained at 45° C. In one compartment 0.06 g of FeCl₃ was dissolved and a carbon electrode inserted. A zinc electrode was immersed in the liquid contained in the other compartment. An Ecochemie PGstat 10 potentiostat was used to measure the potential difference between the electrodes—the maximum recorded value was 1.45V. The half cell reactions for this battery are;

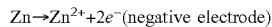

$Zn \rightarrow Zn^{2+} + 2e^-$ (negative electrode)

and,

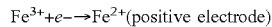

$Fe^{3+} + e^- \rightarrow Fe^{2+}$ (positive electrode)

In the second example 7 ml of 2:1 urea-choline chloride was prepared and divided between the two compartments of a glass cell as before. To one compartment 0.05 ml of Br₂ was added and a carbon electrode was inserted. A zinc electrode was immersed in the liquid contained in the other compartment. The maximum value was 2.14V at 22° C. The half reactions for this battery are;

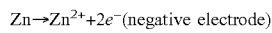

$Zn \rightarrow Zn^{2+} + 2e^-$ (negative electrode)

and,

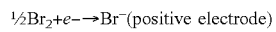

$\tfrac{1}{2}Br_2 + e^- \rightarrow Br^-$ (positive electrode)

EXAMPLE 46

Dissolution of Metal Oxides

An ionic liquid was prepared by heating two molar equivalents of urea with one molar equivalent of choline chloride in a suitable reaction vessel at approximately 70° C. Ruthenium oxide, copper (II) oxide, chromium (VI) oxide, vanadium pentoxide, lead (IV) oxide, manganese (IV) oxide and zinc oxide were all found to be soluble in the ionic liquid, in the temperature range 60° C. to 120° C. None of the oxides of iron or aluminium have shown significant solubility in the ionic liquids and hence these ionic liquids can be used to preferentially extract metal oxides from their ores. The metals can be extracted from the ionic liquids using electrowinning.

The 2:1 urea-choline chloride ionic liquid can also be used to process complex mixtures of metal oxides and allow electrowinning to be used to recover the metals. This property of the ionic liquid and its relatively low bulk cost gives it the potential to be used to treat arc furnace dust on an industrial scale. Electric arc furnace dust containing iron (III) oxide (>30%), zinc oxide (>30%), aluminium oxide (~10%), silica (~5%), calcium oxide (~5%) and lead compounds (~5%) was used in this experiment. Normally it is treated as a waste product and buried in land fill sites. However this is an expensive process and the lead content causes complications due to its high toxicity.

Zinc oxide and lead compounds can be dissolved in 2:1 urea-choline chloride and the respective metals subsequently electrodeposited onto a suitable cathode. Oxides of Fe, Al, Si and Ca were found to be almost totally insoluble in the above ionic liquid. Urea-choline chloride ionic liquid was prepared by combining urea (0.02 moles) with choline chloride (0.01 moles) in a beaker and heating at 80° C. Arc furnace dust (0.5 g) was added to the resulting clear colourless liquid and the mixture was heated at 80° C. for 1 hour. After 1 hour a brown suspension was obtained which was transferred to an electrochemical cell. Metal electrodeposition was achieved using a nickel cathode and a titanium anode (both electrodes were 50 mm by 10 mm and 1 mm thick) and applying a potential difference of 3.5 V for 1 hour. Prior to electrodeposition the electrodes were gently abraded with glass paper and cleaned with acetone. After 1 hour of electrodeposition the nickel cathode was removed from the brown suspension, washed with acetone and dried. A thick charcoal coloured deposit was obtained. The electrodeposited material was analysed using Energy Dispersive Analysis by X-rays. The results of the analysis revealed the presence of lead (77%), zinc (16%) and copper (7%). There was no trace of iron in the deposit thus showing that zinc oxide and iron (III) oxide can be separated and harmful lead compounds removed from arc furnace dust.

Dissolution of Precious Metal Oxides

Other commercially important oxides for reprocessing include processes for the recovery of precious metals, in particular platinum and palladium, from materials in which they are present as oxides. Such mixtures occur, for example, in spent catalyst recovered from automobile catalytic converters. It would be highly desirable to be able to recover such materials in a process which is economically viable. Generally the recovery of such metals from oxide mixtures involves dissolution of the oxide in strong acids, such as aqua regia.

We have discovered that the ionic liquids according to the invention, and in particular those where compound II is a carboxylic acid (preferably oxalic acid) are effective solvents for the dissolution of platinum and palladium oxides. The dissolved metals may be recovered from such solutions by electrowinning. For example, palladium oxide (in the form of spent catalyst supported on various substrates) can be dissolved in the 2:1 oxalic acid-choline chloride ionic liquid. In order to effect the dissolution, the temperature is preferably maintained below 60° C. Palladium metal can subsequently be recovered by deposition onto a variety of substrates.

EXAMPLE 47

An ionic liquid was formed by mixing oxalic acid (17.7 g) and choline chloride (9.8 g) at 60° C. To this a sample of automobile catalyst was added (3.16 g) which was principally PdO on an alumina support. A grey suspension was initially formed which turned into a green solution when the Pd dissolved and the solid precipitated to the base of the cell. The solution was electrolysed using a Ni cathode and a titanium anode and an applied voltage of 5V for 30 min with an approximate current density of 1 mA cm$^{-2}$. At the end of this time a black deposit was obtained on the cathode. This was analysed using energy dispersive analysis by x-rays and found to be primarily Pd metal.

EXAMPLE 48

Metal Electrodeposition

The ionic liquids also find application in metal electrodeposition. Using, for example a 2:1 urea-choline chloride mixture copper, nickel, lead and zinc can be electrodeposited from their chloride salts and this finds application in reprocessing the said metals from industrial waste products.

Four portions of 2:1 urea-choline chloride mixture (0.2 mol urea and 0.1 mol choline chloride) were prepared and heated at 80° C. The preparations were performed in sample tubes. A small quantity (0.001 mol) of a metal-containing compound (either $CuSO_4.5H_2O$, $NiSO_4.6H_2O$, $PbCl_2$ and ZnO) was added to one sample of ionic liquid and left to dissolve. Electrodeposition was then performed in each ionic liquid in turn using Pt electrodes 3 mm in diameter polished with 1 μm $Al_2O_3$ paste. In each experiment a potential difference of 3V was applied for 10 min and the temperature was maintained at 80° C. For each of the metals, characteristic deposits were obtained on the negative Pt electrode.

2:1 urea-choline chloride ionic liquid (16 ml) was prepared by combining the reactants in a beaker and heating at 80° C. Cobalt (II) chloride hexahydrate (1.5% wt) was added to the clear colourless ionic liquid and dissolved to give a blue liquid. The blue liquid was then poured into a PTFE electrochemical cell of internal dimensions 41 mm long, 16 mm wide and 32 mm deep. A mild steel plate and a stainless steel plate, both 55 mm by 40 mm and 1 mm thick, were gently abraded with glass paper, cleaned with acetone and flame annealed. The steel plates were then placed parallel to each other along the inner lengths of the PTFE electrochemical cell. Cobalt deposition was achieved by connecting the mild steel and stainless steel plates to the negative and positive terminals respectively of a Thurlby Thander power pack. A potential was applied and adjusted so as to maintain a current density of 2 mAcm$^{-2}$ for 30 minutes. An ISO-TECH IDM 66 Digital Voltmeter connected in series was used to monitor the current. The experiment was carried out at 60° C. After 30 minutes the mild steel plate was removed from the cell, rinsed with acetone and dried. With a current density of 2 mAcm$^{-2}$ a semi-bright pale grey/brown homogenous deposit was obtained.

A separate portion of 2:1 urea-choline chloride ionic liquid (~5 ml) containing cobalt (II) chloride hexahydrate (1.5% wt) was prepared and poured into an electrochemical cell at 60° C. Voltammetry was performed using a platinum microelectrode (10 μm diameter), a platinum counter electrode and a cobalt reference electrode. An Autolab PGSTAT12 Potentiostat controlled by GPES software was used to carry out the cyclic voltammetry.

Reactions in Ionic Liquids

Heck Reaction

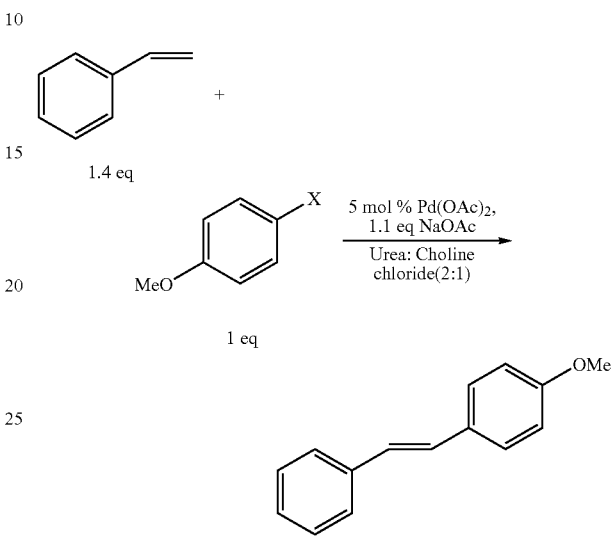

X = I, Br, Cl

The reaction between styrene and 4-iodoanisole in the presence of Pd(OAc)$_2$ and NaOAc at 130° C. for 2 days gave 4-Iodoanisole with a 60% conversion to the product. Using 4-Bromoanisole gave 50% conversion to the product after 2 days under the same reaction conditions. 4-Chloroanisole did not react with styrene under similar conditions.

Using PdCl$_2$ as the catalyst the reaction is faster giving a 90% yield of the same product in 1.5 days.

When Na$_2$CO$_3$ is used as the base instead of NaOAc with PdCl$_2$ as the catalyst, the reaction time decreased and yield improved with 4-iodoanisole giving product with 96% yield in 16 h. After removal of the product by distillation, the same melt and PdCl$_2$ catalyst (with the addition of more Na$_2$CO$_3$) was reused for the same reaction, giving product in 90% yield.

Polymerisation Reactions in Ionic Liquids

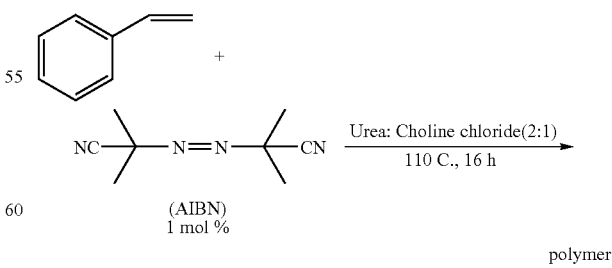

This reaction yielded a polymer with a number average molecular weight of 12,000 with a polydispersity index of 3.2

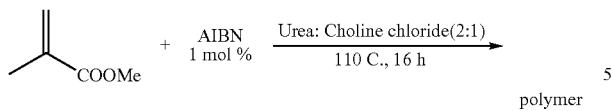

polymer

This reaction yielded a polymer with a number average molecular weight of 12,800 with a polydispersity index of 3.2

Stainless Steel Electropolishing Using 2:1 Urea-Choline Chloride Ionic Liquid

Urea and choline chloride in a molar ratio of 2:1 (160 ml in total) were combined in a beaker and heated at 80° C. until a clear colourless liquid was obtained. The ionic liquid was then poured into a cylindrical electrochemical cell (internal diameter of 80 mm) suspended in an oil bath at 60° C. A zinc sheet was gently abraded using glass paper, degreased with acetone, shaped into a cylinder with a diameter of about 78 mm and slid into the electrochemical cell. The zinc electrode was then connected to the negative terminal of a Thurlby Thander power pack. A stainless steel collar, approximately 40 mm in diameter, was suspended in the centre of the 2:1 urea-choline chloride ionic liquid with the aid of a lead connected to the positive terminal of the Thurlby Thander power pack. A potential difference of 12 V was applied for 6 minutes after which time the stainless steel collar was removed from the ionic liquid, rinsed with acetone and dried. The stainless steel collar was found to be bright and reflective all over its surface. The procedure was repeated using other stainless steel collars and stainless steel fasteners of similar dimension and each time bright reflective finishes were obtained.

Stainless Steel Electropolishing Using 2:1 Ethanediol-choline Chloride

Ethanediol and choline chloride in a molar ratio of 2:1 (20 ml) were combined in a beaker and heated at 80° C. until a clear colourless liquid was obtained. The ionic liquid was then poured into an aluminium electrochemical cell (internal length of 60 mm, internal width of 10 mm and internal depth of 40 mm) suspended in an oil bath at 25° C. The outer wall of the aluminium cell was connected to the negative terminal of a Thurlby Thander power pack. A stainless steel plate, 50 mm by 10 mm and 1 mm thick, was degreased and suspended in the centre of the aluminium cell with the aid of a lead connected to the positive terminal of the Thurlby Thander power pack. A potential difference was applied and adjusted so as to maintain a current density between 60 and 70 mAcm$^{-2}$ at the stainless steel plate for 6 minutes. After 6 minutes the stainless steel plate was removed from the 2:1 ethanediol-choline chloride ionic liquid, rinsed with acetone and dried. The stainless steel plate was found to be bright and reflective all over its surface. The 2:1 ethanediol-choline chloride ionic liquid can be modified by the addition of lithium chloride (5% wt). The increased chloride content of the ionic liquid increases the conductivity and thus lowers the power consumption during electropolishing. Stainless steel polished in 2:1 ethanediol-choline chloride containing lithium chloride is also very bright and reflective.

The invention claimed is:

1. An ionic compound, having a freezing point of up to 100° C. formed by the reaction of at least one amine salt of the formula $$R^1R^2R^3R^4N^+X^-$$ (I)

with at least one organic compound (II) which is capable of forming a hydrogen bond with X$^-$, wherein R$^1$, R$^2$, R$^3$ and R$^4$ are each independently:-
H,
optionally substituted C$_1$ to C$_5$ alkyl,
optionally substituted C$_6$ to C$_{10}$ cycloalkyl,
optionally substituted C$_6$ to C$_{12}$ aryl
optionally substituted C$_7$ to C$_{12}$ alkaryl, or wherein R$^1$ and R$^2$ taken together represent a C$_4$ to C$_{10}$ optionally substituted alkylene group, thereby forming with the N atom of formula (I) a 5 to 11-membered heterocyclic ring, X$^-$, is NO$_3^-$, F$^-$, Cl$^-$, Br$^-$, I$^-$, BF$_4^-$, ClO$_4^-$, CN$^-$, SO$_3$CF$_3^-$, or COOCF$_3^-$, and wherein the term "optionally substituted" means that the group in question may or may not be substituted with one or more groups selected from OH, SH, SR$^5$, Cl, Br, F, I, NH$_2$, CN, NO$_2$, COOR$^5$, CHO, COR$^5$ and OR$^5$, wherein R$^5$ is a C$_1$ to C$_{10}$ alkyl or cycloalkyl group,
wherein all of R$^1$, R$^2$, R$^3$ and R$^4$ are not identical, and
wherein compound (II) is a compound of the formula R$^6$COOH, R$^7$R$^8$NH, R$^9$CZNH$_2$, or R$^{10}$OH, wherein:-
R$^6$, R$^7$, R$^8$, R$^{10}$ are each H, a C$_1$–C$_8$ alkyl group, an aryl group, or a C$_7$–C$_{12}$ alkaryl group optionally substituted with from 0 to 6 group selected from OH, SR$^5$, Cl, Br, F, I, NH$_2$, CN, NO$_2$, COOR$^5$, COR$^5$ and OR$^5$, wherein R$^5$ is H, a C$_1$–C$_{10}$ alkyl or cycloalkyl group, R$^9$ is a C$_1$–C$_8$ alkyl group, C$_1$–C$_{12}$ an aryl group, or a C$_7$–C$_{12}$ alkaryl group optionally substituted with from 0 to 6 groups selected from OH, SR$^5$, Cl, Br, F, I, NH$_2$, CN, NO$_2$, COOR$^5$, COR$^5$ and OR$^5$, wherein R$^5$ is H, a C$_1$ to C$_{10}$ alkyl or cycloalkyl group, or wherein R$^9$ is NHR$^{11}$, wherein R$^{11}$ is H or a C$_1$–C$_6$ alkyl group, and Z is O and wherein formula (I) and compound (II) are utilized in a molar ration from 1:1.5 to 1:2.5

2. The ionic compound of claim 1, wherein compound (II) is an organic compound which is solid at 20° C.

3. The ionic compound of claim 1, wherein compound (II) is urea, acetamide, glyoxylic acid, malonic acid, oxalic acid dihydrate, trifluoroacetic acid, benzoic acid, benzyl alcohol, phenol p-methyl phenol, o-methyl phenol, m-methyl phenol, p-chloro phenol, D-fructose, or vanillin.

4. The ionic compound of claim 1, wherein compound (II) is urea, aniline or a substituted aniline, a C$_1$–C$_6$ hydroxy-aliphatic acid, or a dicarboxylic acid of the formula HOOC (CH$_2$)$_n$COOH, wherein n is 0 or 1, acetamide, a phenol or a substituted phenol, an alkylene glycol, or citric acid.

5. The ionic compound of claim 1, wherein compound (II) is urea, acetamide; oxalic acid dihydrate, phenol, ethylene glycol, or citric acid.

6. The ionic compound of claim 1, wherein compound (II) has a freezing point of less than 160° C.

7. The ionic compound of claim 5, wherein compound (II) has a freezing point of 20° C. or less.

8. The ionic compound of claim 1, wherein compound (II) contains only one type of functional group capable of acting as hydrogen bond donor.

9. The ionic compound of claim 1, wherein the molar ratio of formula (I) to compound (II) is about 1:2.

10. The ionic compound of claim 1, wherein R$^4$ is a C$_1$ to C$_{10}$ alkyl or a cycloalkyl group, substituted with at least one group selected from OH, Cl, Br, F, I, NH$_2$, CN, NO$_2$, COOR$^5$, COR$^5$, CHO and OR$^5$.

11. The ionic compound of claim 1, wherein each of R$^1$, R$^2$, R$^3$, independently is a C$_1$–C$_5$ alkyl or a cycloalkyl group, and R$^4$ is hydroxyl-alkyl.

12. The ionic compound of claim 7, wherein each of R$^1$, R$^2$, R$^3$, is methyl, and R$^4$ is hydroxyethyl.

13. The ionic compound of claim 1, wherein X⁻ is chloride.

14. The ionic compound of claim 1, wherein $R^1$, $R^2$, $R^3$, and $R^4$ have the one of following meanings

| $R^1$ | $R^2$ | $R^3$ | $R^4$ |
|---|---|---|---|
| Me | Me | Me | $C_2H_4OH$ |
| Me | Me | Benzyl | $C_2H_4OH$ |
| Me | Me | Et | $C_2H_4OH$ |
| Me | Me | Me | Benzyl |
| Me | Me | Me | $C_2H_4OCOMe$ |
| Me | Me | Me | $C_2H_4Cl$ |
| Me | Me | Me | $ClCH_2CHOHCH_2$ (R) |
| Me | Me | Me | $ClCH_2CHOHCH_2$ (S) |
| Me | H | H | H |
| Me | Me | H | H |
| Et | Et | Et | H |
| Et | Et | Et | Benzyl |
| Me | Benzyl | $C_2H_4OH$ | $C_2H_4OH$ |
| Me | H | H | $CH_2COOH$ |
| Me | Me | Me | $BrC_2H_4$ |
| Me | Me | Me | $C_2H_4F$ |
| Me | Me | Me | $Me(CH_2)_{11}$ |
| Et | Et | Et | Me |
| ET | Et | Et | Benzyl |
| Me | Me | $C_2H_4OH$ | $C_2H_4OH$ |

15. A method of preparing an ionic compound, having a freezing point of up to 100° C., which method comprises reacting at least one amine salt of the formula $$R^1R^2R^3R^4N^+X^- \qquad (I)$$

with at least one organic compound (II) which is capable of forming a hydrogen bond with X⁻, wherein $R^1$, $R^2$, $R^3$ and $R^4$ are each independently:-
H,
optionally substituted $C_1$ to $C_5$ alkyl,
optionally substituted $C_6$ to $C_{10}$ cycloalkyl,
optionally substituted $C_6$ to $C_{12}$ aryl,
optionally substituted $C_7$ to $C_{12}$ alkaryl, or wherein
$R^1$ and $R^2$ taken together represent a $C_4$ to $C_{10}$ optionally substituted alkylene group, thereby forming with the N atom of formula (I) a 5 to 11-membered heterocyclic ring, X⁻ is $NO_3^-$, F⁻, Cl⁻, Br⁻, I⁻, $BF_4^-$, $ClO_4^-$, CN⁻, $SO_3CF_3^-$, or $COOCF_3^-$, and wherein the term "optionally substituted" means that the group in question may or may not be substituted with one or more groups selected from OH, SH, $SR^5$, Cl, Br, F, I, $NH_2$, CN, $NO_2$, $COOR^5$, CHO, $COR^5$ and $OR^5$, wherein $R^5$ is a $C_1$ to $C_{10}$ alkyl or cycloalkyl group,
wherein all of $R^1$, $R^2$, $R^3$ and $R^4$ are not identical, and
wherein compound (II) is a compound of the formula $R^6COOH$, $R^7R^8NH$, $R^9CZNH_2$, or $R^{10}OH$, wherein:-
$R^6$, $R^7$, $R^8$, $R^{10}$ are each H, a $C_1$–$C_8$ alkyl group, an aryl group, or a $C_7$–$C_{12}$ alkaryl group optionally substituted with from 0 to 6 groups selected from OH, $SR^5$, Cl, Br, F, I, $NH_2$, CN, $NO_2$, $COOR^5$, $COR^5$ and $OR^5$, wherein $R^5$ is H, a $C_1$ to $C_{10}$ alkyl or cycloalkyl group, $R^9$ is a $C_1$–$C_8$ alkyl group, $C_1$–$C_{12}$ an aryl group, or a $C_7$–$C_{12}$ alkaryl group optionally substituted with from 0 to 6 groups selected from OH, $SR^5$, Cl, Br, F, I, $NH_2$, CN, $NO_2$, $COOR^5$, $COR^5$ and $OR^5$, wherein $R^5$ is H, a $C_1$ to $C_{10}$ alkyl or cycloalkyl group, or wherein $R^9$ is $NHR^{11}$, wherein $R^{11}$ is H or a $C_1$–$C_6$ alkyl group, and Z is O and wherein formula (I) and compound (II) have a molar ratio from 1:1.5 to 1:2.5.

16. The method of claim 15, further comprising heating the amine salt of formula (I) with the compound (II).

17. A method of recovering a metal from a metal oxide, which method comprises forming a solution of the metal oxide in the ionic compound of claim 1, and electrolysing the solution to recover the metal.

18. The method of claim 17, wherein the metal is platinum or palladium.

19. A method of electropolishing a metal article, which method comprises immersing the metal article in the ionic compound of claim 1, and applying a voltage to the metal article to electropolish the metal.

20. A method of forming a solution of a solute, which method comprises dissolving the solute in an ionic compound having a freezing point of up to 100° C., the said ionic compound being formed by the reaction of at least one amine salt of the formula $$R^1R^2R^3R^4N^+X^- \qquad (I)$$

with at least one organic compound (II) which is capable of forming a hydrogen bond with X⁻, wherein $R^1$, $R^2$, $R^3$ and $R^4$ are each independently:-
H,
optionally substituted $C_1$ to $C_5$ alkyl,
optionally substituted $C_6$ to $C_{10}$ cycloalkyl,
optionally substituted $C_6$ to $C_{12}$ aryl,
optionally substituted $C_7$ to $C_{12}$ alkaryl, or wherein
$R^1$ and $R^2$ taken together represent a $C_4$ to $C_{10}$ optionally substituted alkylene group, thereby forming with the N atom of formula (I) a 5 to 11-membered heterocyclic ring, X⁻ is $NO_3^-$, F⁻, Cl⁻, Br⁻, I⁻, $BF_4^-$, $ClO_4^-$, CN⁻, $SO_3CF_3^-$, or $COOCF_3^-$, and wherein the term "optionally substituted" means that the group in question may or may not be substituted with one or more groups selected from OH, SH, $SR^5$, Cl, Br, F, I, $NH_2$, CN, $NO_2$, $COOR^5$, CHO, $COR^5$ and $OR^5$, wherein $R^5$ is a $C_1$ to $C_{10}$ alkyl or cycloalkyl group,
wherein all of $R^1$, $R^2$, $R^3$ and $R^4$ are not identical, and
wherein compound (II) is a compound of the formula $R^6COOH$, $R^7R^8NH$, $R^9CZNH_2$, or $R^{10}OH$, wherein:-
$R^6$, $R^7$, $R^8$, $R^{10}$ are each H, a $C_1$–$C_8$ alkyl group, an aryl group, or a $C_7$–$C_{12}$ alkaryl group optionally substituted with from 0 to 6 groups selected from OH, $SR^5$, Cl, Br, F, I, $NH_2$, CN, $NO_2$, $COOR^5$, $COR^5$ and $OR^5$, wherein $R^5$ is H, a $C_1$ to $C_{10}$ alkyl or cycloalkyl group, $R^9$ is a $C_1$–$C_8$ alkyl group, $C_1$–$C_{12}$ an aryl group, or a $C_7$–$C_{12}$ alkaryl group optionally substituted with from 0 to 6 groups selected from OH, $SR^5$, Cl, Br, F, I, $NH_2$, CN, $NO_2$, $COOR^5$, $COR^5$ and $OR^5$, wherein $R^5$ is H, a $C_1$ to $C_{10}$ alkyl or cycloalkyl group, or wherein $R^9$ is $NHR^{11}$, wherein $R^{11}$ is H or a $C_1$–$C_6$ alkyl group, and Z is O and wherein formula (I) and compound (II) have a molar ratio from 1:1.5 to 1:2.5.

* * * * *

UNITED STATES PATENT AND TRADEMARK OFFICE
CERTIFICATE OF CORRECTION

| | | |
|---|---|---|
| PATENT NO. | : 7,183,433 B2 | |
| APPLICATION NO. | : 10/381060 | |
| DATED | : February 27, 2007 | |
| INVENTOR(S) | : Abbott et al. | |

It is certified that error appears in the above-identified patent and that said Letters Patent is hereby corrected as shown below:

Column 14:
    In claim 4, line 2, after "aniline or a substituted aniline," add --a $C_1$-$C_6$ aliphatic acid,--

Column 15:
    In claim 15, line 4, replace "$R^1R^2R^3R^4N^{+X-}$" with --$R^1R^2R^3R^4N^+X^-$--

Column 16:
    In claim 20, line 6, replace "$R^1R^2R^3R^4N^{+X-}$" with --$R^1R^2R^3R^4N^+X^-$--

Signed and Sealed this

First Day of May, 2007

JON W. DUDAS
*Director of the United States Patent and Trademark Office*